(12) United States Patent
Meller et al.

(10) Patent No.: US 6,247,928 B1
(45) Date of Patent: *Jun. 19, 2001

(54) DISPOSABLE ANESTHESIA DELIVERY SYSTEM

(75) Inventors: Moshe Meller, 20 Rachel Street, Haifa 34402 (IL); Michael Feldman, Toms River, NJ (US)

(73) Assignee: Moshe Meller, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/165,010

(22) Filed: Jun. 15, 1998

Related U.S. Application Data

(60) Provisional application No. 60/081,204, filed on Apr. 9, 1998.

(51) Int. Cl.[7] ............................................. A61G 17/02
(52) U.S. Cl. .......................... 433/80; 433/165; 604/239; 606/80
(58) Field of Search .............................. 433/80, 81, 82, 433/134, 165; 604/51, 239, 267; 606/80; 600/567

(56) References Cited

U.S. PATENT DOCUMENTS

| Re. 27,923 | 2/1974 | Bentov | 604/507 |
|---|---|---|---|
| 1,123,730 | 1/1915 | Greenfield | 433/165 |
| 1,539,637 | 5/1925 | Bronner | 433/81 |
| 2,317,648 | 4/1943 | Siqveland | 433/80 |

(List continued on next page.)

FOREIGN PATENT DOCUMENTS 1430092  3/1976  (GB).

OTHER PUBLICATIONS

Pearce, Jr. "Intraosseous Injection For Profound Anesthesia of the Lower Molar" (1 page).
Cannell et al "Intraosseous Injections of Lignocaine Local Anaesthetics" British Dental Journal, vol. 141, Jul. 20, 1976; pp. 48–50.

(List continued on next page.)

*Primary Examiner*—John J. Wilson
(74) *Attorney, Agent, or Firm*—Frishauf, Holtz, Goodman, Langer & Chick, PC

(57) ABSTRACT

An intraosseous delivery apparatus having a drill coupling member and a drilling needle member. The drill coupling member includes a shaft, an open housing provided at one end of the shaft, a connecting portion provided at an opposite end of the shaft for establishing a connection to a conventional dental drill, and an anticlog needle extending from the shaft through the open housing. The drilling needle member includes a drilling needle housing and a hollow drilling needle shaft extending therefrom. The drilling needle member is adapted to be removably engaged with the drill coupling member such that the drilling needle housing of the drilling needle member is inserted into the open housing of the drill coupling member and such that the anticlog needle of the drill coupling member is inserted into the hollow drilling needle shaft of the drilling needle member. The drilling needle housing of the drilling needle member and the open housing of the drill coupling member are shaped so that a bone penetration force may be applied therebetween for drilling a hole in a bone to insert the drilling needle member therein when the drilling needle member and the drill coupling member are engaged. The hollow drilling needle shaft is adapted to receive a needle of a syringe when the drilling needle member and the drill coupling member are disengaged and the drilling needle member is left inserted in the hole drilled in the bone, so that a reusable communication path through the hollow drilling needle shaft directly into the hole drilled in the bone is established through which fluid may be repeatedly injected.

22 Claims, 7 Drawing Sheets

U.S. PATENT DOCUMENTS

| | | | |
|---|---|---|---|
| 2,442,033 | 5/1948 | Brantly et al. | 433/82 |
| 3,406,685 | 10/1968 | May | 604/164.11 |
| 3,750,667 | 8/1973 | Pshenichny et al. | 604/117 |
| 3,778,904 | 12/1973 | Melde | 433/120 |
| 3,893,445 | 7/1975 | Hofsess | 600/567 |
| 4,002,169 | 1/1977 | Cupler, II | 604/22 |
| 4,021,920 | 5/1977 | Kirschner et al. | 433/82 |
| 4,193,197 | 3/1980 | Kuris et al. | 433/82 |
| 4,220,446 | 9/1980 | Walker | 433/85 |
| 4,306,570 | 12/1981 | Matthews | 128/754 |
| 4,513,754 | 4/1985 | Lee | 128/753 |
| 4,678,471 | 7/1987 | Noble et al. | 623/16 |
| 4,747,824 | 5/1988 | Spinello | 604/51 |
| 4,787,893 | 11/1988 | Villette | 604/188 |
| 4,869,717 * | 9/1989 | Adair | 604/51 |
| 4,944,677 | 7/1990 | Alexandre | 433/165 |
| 4,973,247 | 11/1990 | Varnes et al. | 433/85 |
| 5,049,150 | 9/1991 | Cozad | 606/86 |
| 5,057,013 | 10/1991 | Dillon | 433/165 |
| 5,085,631 | 2/1992 | Leighton | 604/28 |
| 5,201,656 | 4/1993 | Sicurelli, Jr. | 433/82 |
| 5,203,866 * | 4/1993 | Islam | 604/239 |
| 5,261,877 | 11/1993 | Fine et al. | 604/49 |
| 5,275,563 | 1/1994 | Cohen et al. | 433/224 |
| 5,312,345 | 5/1994 | Cole | 604/110 |
| 5,312,375 | 5/1994 | Gurmarnik | 604/264 |
| 5,341,816 | 8/1994 | Allen | 128/754 |
| 5,374,270 | 12/1994 | McGuire et al. | 606/86 |
| 5,389,070 * | 2/1995 | Morell | 604/51 |
| 5,406,940 | 4/1995 | Melzer et al. | 128/6 |
| 5,423,823 | 6/1995 | Schmeiding | 606/80 |
| 5,423,824 | 6/1995 | Akerfeldt et al. | 606/80 |
| 5,429,504 | 7/1995 | Peltier et al. | 433/165 |
| 5,431,655 | 7/1995 | Melker et al. | 606/79 |
| 5,484,442 | 1/1996 | Melker et al. | 606/79 |
| 5,489,208 | 2/1996 | Mandell | 433/165 |
| 5,554,154 | 9/1996 | Rosenburg | 606/80 |
| 5,601,559 | 2/1997 | Melker et al. | 606/79 |
| 5,762,639 * | 6/1998 | Gibbs | 606/80 |
| 5,779,708 | 7/1998 | Wu | 606/80 |
| 5,814,049 * | 9/1998 | Pratt et al. | 606/80 |

OTHER PUBLICATIONS

Lilienthal "A Clinical Appraisal of Intraosseous Dental Anesthesia", Oral Surg. vol. 39, No. 5, May, 1975, pp. 692–697.

Bourke "Intra–Osseous Anaesthesia", Dent. Anaesthesia And Sedation, vol. 3, No. 2, Jul. 1974, pp. 13–18.

Dorfman "Predictable and Effective Anesthesia Utilizing Intraosseous Injections".

Leonard "The Efficacy of an Intraosseous Injection System of Delivering Local Anesthetic".

Magnes "Intraosseous Anesthesia", Anesthesia Progress, Nov. 1968 pp. 264–267.

Garfunkel et al. "Intraligamentry–Intraosseous Anesthesia", Int. J. Oral Surg. 1983; 12: pp. 334–339.

Biddulph "Intraosseous Anesthesia For Dental Procedures", The Arizona Dental Journal.

* cited by examiner

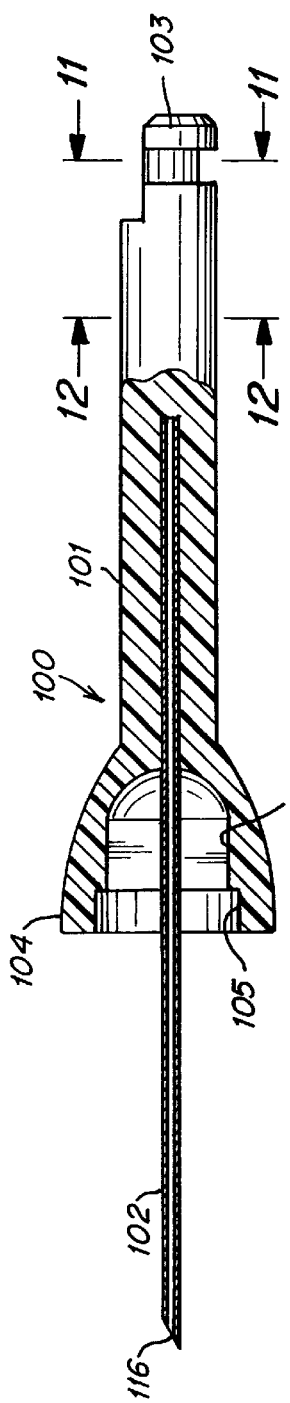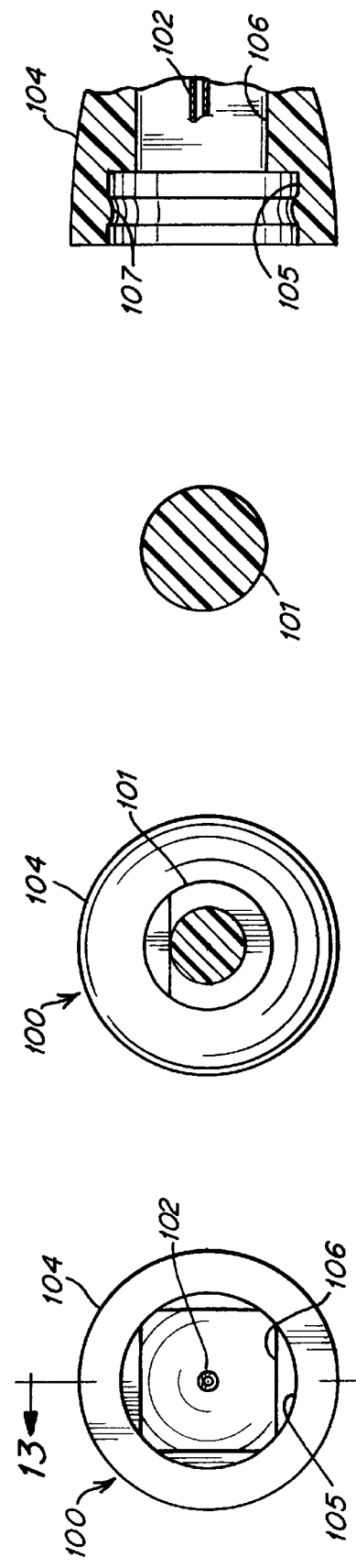

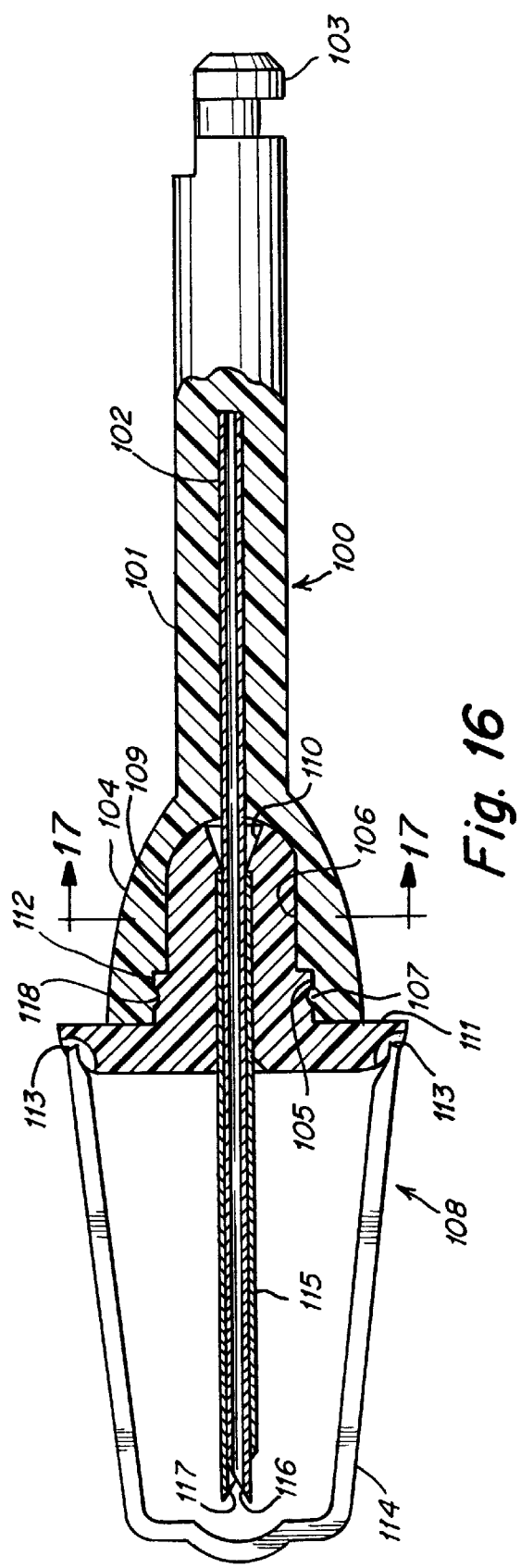
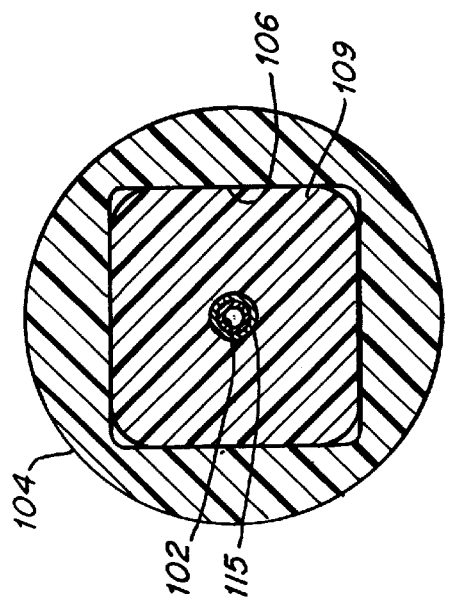

DISPOSABLE ANESTHESIA DELIVERY SYSTEM

CROSS REFERENCE TO RELATED APPLICATION

This application claims the benefit of Provisional application Ser. No. 60/081,204, filed Apr. 9, 1998, the priority of which is claimed, and the entire contents of which are incorporated herein by reference.

BACKGROUND OF THE INVENTION

The present invention relates to a disposable delivery system for delivering anesthesia. In particular, the present invention relates to a disposable delivery apparatus and method for intraosseously delivering dental anesthesia or anesthesia to other parts of a living body.

The present invention is described in detail below with respect to application of dental anesthesia, but the invention is applicable to delivery of anesthesia or other fluids to other parts of a living body, either human or animal. By describing the invention in detail with respect to delivery of dental anesthesia, the invention is not limited to use only in connection with dental procedures.

Dental anesthesia is generally delivered by injection of a topical anesthetic followed by a deeper injection of anesthetic for desensitizing nerve endings within the region of interest (infiltration) or for blocking off remote sensory nerves which are coupled to the region of interest (nerve blocking).

It is extremely desirable to minimize the amount of anesthesia injected because toxic reactions may result from drug sensitivity or misdirection of the injection needle into the bloodstream. Such risk of toxic reaction is heightened when repeated administration of anesthesia as required, as is often the case with conventional delivery techniques. In addition, conventional administration of anesthesia generally results in numbness of the tongue, cheek, lips and/or even part of the face of the patient for some time after a dental procedure.

As set forth in U.S. Pat. No. 4,944,677 to Alexandre, conventional methods of delivering dental anesthesia include injection into mucous tissue, injection into a ligament, injection into the septum and injection near a nerve-trunk. However, injection into mucous tissue is disadvantageous because it takes a long time for the anesthesia to take effect (about 5 minutes), because the amount of anesthesia is high (about 4 cc), and because adrenalin or another vaso conductor is required for cardiac patients. Injection into a ligament is disadvantageous because it requires high pressure for injection (which causes pain), because injection is into a septic area, because the risk of infection of the ligament is increased, and because the risk of post-operative problems including inflammation and necrosis is increased. Injection into the septum is disadvantageous because it also requires high pressure for injection (which causes pain), because exact positioning of the needle is required, and because injection is into a septic area. And finally, injection into near the nerve-trunk is disadvantageous because there is a long delay in effecting anesthesia (about 10 minutes), because there is a high risk of inadvertent injection into a blood vessel, and because post-operative numbness is very long lasting.

Intraosseous delivery of dental anesthesia directly into the jawbone is also known. Intraosseous delivery is extremely advantageous because it very rapidly achieves numbness limited only to the tooth to be treated, because it enables the amount of anesthetic to be significantly reduced, and because postoperative numbness is essentially avoided.

U.S. Pat. No. 1,539,637 to Bronner discloses a dental instrument adapted for use in penetrating bone structures in order to provide drainage or to inject anesthetics or other fluids. The dental instrument of Bronner essentially comprises a chuck to which a hollow drill may be connected. The dental instrument includes a slidable cleaning pin for preventing cuttings from entering a passage in the hollow drill during bone penetration. Once the hollow drill has penetrated the bone, a syringe is coupled to the dental instrument in order to inject fluid such as an anesthetic. The pressure of the injected fluid causes the cleaning pin to be withdrawn from the interior of the hollow drill to thereby permit the flow of fluid through the passage in the hollow drill into the interior of the bone. The dental instrument of Bronner, however, is cumbersome and cannot remain in place during the performance of a dental procedure, and also does not enable simple re-injection of anesthetic, if and when required, during the performance of a dental procedure.

U.S. Pat. No. 2,317,648 to Siqveland discloses an intraosseous delivery apparatus and method whereby a threaded sleeve is concentrically and removably positioned around a drill bit. The drill bit and threaded sleeve are used together to penetrate the bone, and then the drill bit is detached and withdrawn, leaving the threaded sleeve embedded in the bone as a guide for a hypodermic needle through which anesthesia may be injected. After injection of anesthesia, the threaded sleeve is withdrawn from the bone by reverse rotation. This technique, however, is cumbersome and exacting in that it requires that three small separate elements (i.e., the threaded sleeve, the drill bit and the hypodermic needle) be connected and disconnected during utilization.

U.S. Pat. No. 4,944,677 to Alexandre discloses an intraosseous delivery apparatus and method whereby a smooth, hollow drilling needle is used to drill a hole into the jawbone near the apex of a tooth to be anesthetized. The drilling needle is then removed from the jawbone and a hypodermic needle of substantially the same gauge as the drilling needle is then inserted into the hole formed in the jawbone using a single drop of blood formed during drilling as a marker for entrance to the hole. After the hypodermic needle is inserted into the hole, anesthesia is then delivered by injection directly into the jawbone. This technique, however, is disadvantageous because in actual practice it is very difficult to find the drilled hole and insert the hypodermic needle therein.

U.S. Pat. No. 5,431,655, U.S. Pat. No. 5,484,442 and U.S. Pat. No. 5,601,559, which are related patents and which are all to Melker et al, disclose an intraosseous needle for delivering dental anesthesia. The intraosseous needle has a threaded shaft with a passageway extending substantially therethrough, a solid pointed tip with cutting edges for boring through bone, and two side ports communicating with the passageway. A hub is provided for coupling the needle to a gripping device, and a handle is provided in the shape of a ball knob and is adapted to telescopically and grippingly receive the hub of the needle. The hub and handle are both equipped with mutually engaging torque-transmitting surfaces. After the needle is inserted into the jawbone, anesthesia is delivered via the passageway through the two side ports. This technique, however, avoids the use of a dental drill.

SUMMARY OF THE INVENTION

It is an object of the present invention to provide a disposable delivery apparatus and method for intraosseously delivering dental anesthesia in a simple, easy and effective manner. In particular, it is an object of the present invention to provide a disposable delivery apparatus and method for intraosseously delivering dental anesthesia which takes advantage of the power of a conventional dental drill for a creating sufficient force to achieve simple, easy and effective penetration of the jawbone, and which enables a direct communication path into the jawbone to be simply, easily and effectively established. In addition, it is also an object of the present invention to provide a disposable delivery apparatus and method for intraosseously delivering dental anesthesia which achieves a direct, reusable communication path into the jawbone or tooth so that additional anesthetic can be delivered, if and when necessary, during performance of a dental procedure.

In order to achieve the above objects, an intraosseous delivery apparatus according to a first embodiment of the present invention comprises a housing having a delivery opening through which a fluid may be introduced, and a drilling needle shaft extending from the housing. The housing is shaped to be removably or detachably coupled to a dental drill (handpiece) for providing a bone penetration force, and the drilling needle shaft has a cutting edge for drilling a hole in a bone. The drilling needle shaft has a passageway provided therein which communicates with the delivery opening for delivering the fluid introduced into the housing directly into the hole drilled in the bone. In addition, a cap is provided for liquid tightly engaging with the housing. The cap includes a nozzle to which a flex tube may be engaged, and the nozzle communicates with the delivery opening in the housing when the cap and the housing are engaged so as to establish a communication path from the flex tube through the nozzle into the housing and through the passageway provided in the drilling needle shaft directly into the hole drilled in the bone. Still further, a removable anticlog plunger is provided which has an anticlog pin extending therefrom. The anticlog plunger is insertable into the housing such that the anticlog pin fills the passageway in the drilling needle shaft and so that when the drilling needle shaft drills the hole in the bone, the anticlog pin prevents debris from entering into the passageway.

According to a second embodiment of the present invention, an intraosseous delivery apparatus according to a second embodiment of the present invention comprises a drill coupling member and a drilling needle member. The drill coupling member includes a shaft, an open housing provided at one end of the shaft, a connecting portion provided at an opposite end of the shaft for establishing a connection to a conventional dental drill, and an anticlog needle extending from the shaft through the open housing. The drilling needle member includes a drilling needle housing and a hollow drilling needle shaft extending therefrom. The drilling needle member is adapted to be removably engaged with the drill coupling member such that the drilling needle housing of the drilling needle member is inserted into the open housing of the drill coupling member and such that the anticlog needle of the drill coupling member is inserted into the hollow drilling needle shaft of the drilling needle member. The drilling needle housing of the drilling needle member and the open housing of the drill coupling member are shaped so that a bone penetration force may be applied therebetween for drilling a hole in a bone to insert the drilling needle member therein when the drilling needle member and the drill coupling member are engaged. The hollow drilling needle shaft is adapted to receive a needle of a syringe when the drilling needle member and the drill coupling member are disengaged and the drilling needle member is left inserted in the hole drilled in the bone, so that a reusable communication path through the hollow drilling needle shaft directly into the hole drilled in the bone is established through which fluid may be repeatedly injected.

BRIEF DESCRIPTION OF THE DRAWINGS

FIG. 9 is a partial sectional view of a drill coupling member according to a second embodiment of the present invention.

FIG. 10 is a left side end view of the drill coupling member shown in FIG. 9.

FIG. 11 is a cross sectional view taken along line 11—11 shown in FIG. 9.

FIG. 12 is a cross sectional view taken along line 12—12 shown in FIG. 9.

FIG. 13 is a cross sectional view taken along line 13—13 shown in FIG. 10.

FIG. 16 is a partial sectional view of the drill coupling member and drilling needle member according to the second embodiment of the present invention in a connected state.

FIG. 17 is a cross sectional view taken along line 17—17 shown in FIG. 16.

DETAILED DESCRIPTION

Figures 1, 2:
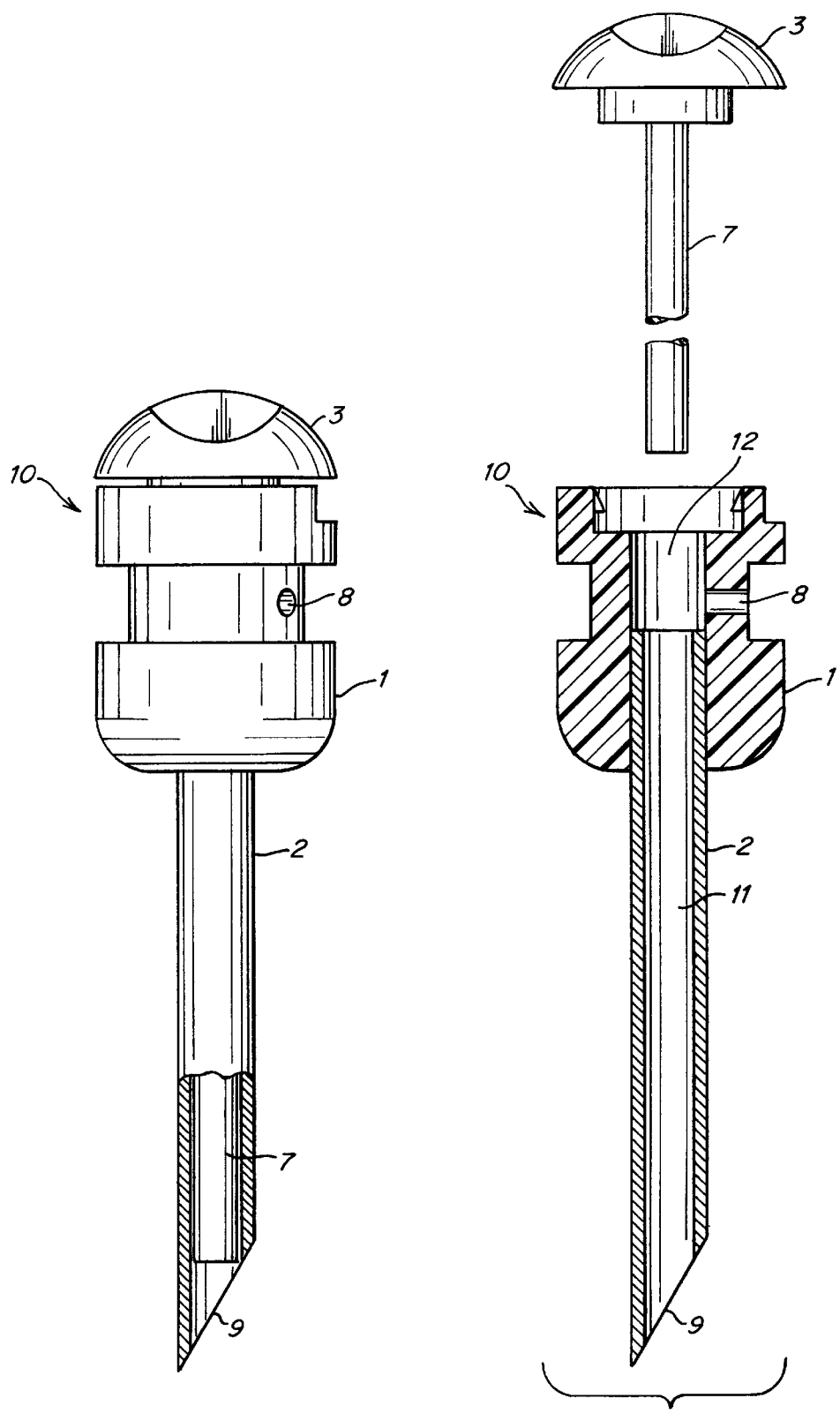
FIG. 1 is a partial perspective view and partial sectional view showing a drilling needle member according to the first embodiment of the present invention prior to use, with an anticlog plunger inserted therein.
FIG. 2 is a sectional view showing the drilling needle member with the anticlog plunger removed therefrom.

As shown in FIGS. 1 and 2, the drilling needle member 10 according to the first embodiment of the present invention comprises a housing 1 disposed on a drilling needle shaft 2, and a removable anticlog plunger 3 having an anticlog pin 7 extending therefrom.

The drilling needle shaft 2 is provided with a cutting edge 9 for penetrating bone. The drilling needle shaft 2 may be made of surgical steel, or the like, of which at least the cutting edge 9 must be of sufficient hardness to drill through bone. The cutting edge 9 is preferably an intradermal medical shape, and the angle of the main surface of the cutting edge is preferably generally about 20° to 30° relative to the vertical in FIG. 1. In addition, the drilling needle shaft 2 is hollow and is provided with a passageway 11 which extends along the entire length thereof. Preferably the needle shaft 2 has an outer diameter of from about 0.4 to 0.6 mm (preferably about 0.6 mm). The inner diameter of the hollow portion ranges from about 0.2 mm for a 0.4 mm outer diameter to about 0.3 mm for a 0.6 mm outer diameter.

The housing 1 may be made of a metal such as surgical steel, or may be made of a substantially rigid plastic such as a polyamide or the like. The housing 1 is provided with a delivery opening 8 which communicates with the passageway 11 in the drilling needle shaft 2 via an interior space 12 within the housing 1. In addition, the housing 1 is shaped so that it may be coupled to a standard contra angle head of a dental drill.

As shown in FIG. 1, prior to use, the anticlog plunger 3 having the anticlog pin 7 extending therefrom is inserted into the housing 1 such that the anticlog pin 7 essentially fills the passageway 11 in the drilling needle shaft 2. Accordingly, when the drilling needle member 10 is used to drill a hole in bone, the anticlog pin 7 prevents debris from entering into the passageway 11 in the drilling needle shaft 2. The anticlog pin 7 may be flexible or rigid, and may be solid or hollow. The distal end of the anticlog pin 7, moreover, may comprise a perpendicular surface as shown in FIG. 1 or a rounded surface, or the distal end of the anticlog pin 7 may have an oblique configuration aligned with or offset from the cutting edge 9 of the drilling needle shaft 2.

As shown in FIG. 2, the anticlog plunger 3 may be removed from the drilling needle member 10 after a hole has been drilled.

Figure 3:
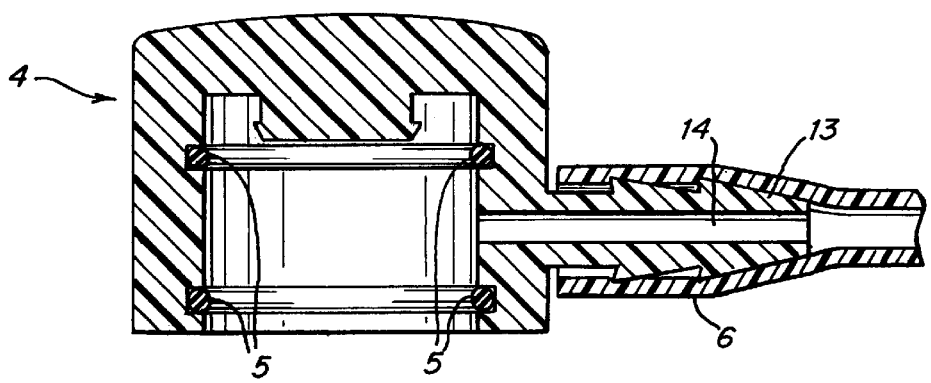
FIG. 3 is a sectional view of a cap for coupling the drilling needle member to a flex tube.

FIG. 3 shows a cap 4 which may be coupled to the housing 1 after the anticlog plunger 3 has been removed from the drilling needle member 10. The cap 4 may be made of a substantially rigid plastic such as a polyamide or the like, and is shaped to be engaged with the housing 1. The cap 4 is provided with a nozzle 13 having a passageway 14 therein. A flex tube 6 may be engaged with the nozzle 13 in a liquid tight manner so that an interior of the flex tube 6 communicates with the passageway 14 in the nozzle 13. The cap 4 may also include seals 5.

Figure 4:
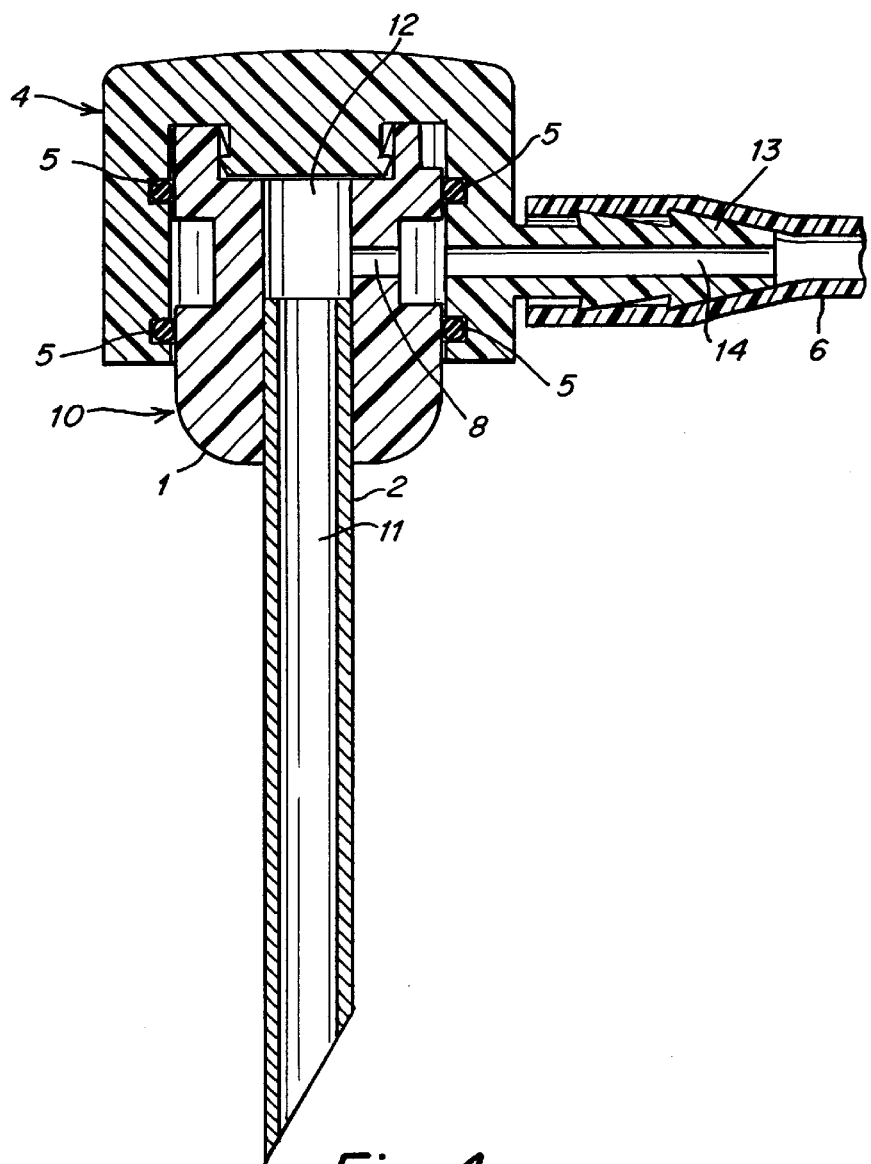
FIG. 4 is a sectional view of the drilling needle member, with the cap thereon and coupled to a flex tube.

As shown in FIG. 4, when the cap 4 is engaged with the housing 1, the seals 5 contact respective outer surfaces of the housing 1 to thereby ensure a liquid tight engagement between the cap 4 and the housing 1. In addition, the cap 4 is configured so that the passageway 14 in the nozzle 13 thereof communicates with the delivery opening 8 in the housing 1 when the cap 4 is engaged with the housing 1. Accordingly, a continuous liquid tight communication path can be established from the flex tube 6 through the passageway 14 in the nozzle 13 into the delivery opening 8 of the housing 1 and through the interior space 12 of the housing 1 into the passageway 11 in the drilling needle shaft 2, so that anesthesia may be delivered via this communication path directly into a hole drilled in the jawbone of a patient by the drilling needle member 10.

FIGS. 5–8 show the drilling needle apparatus of the first embodiment in use during respective procedural steps according to a method of the present invention. Preliminarily, the gingiva 16 attached to the jawbone 17 at a desired location may first be anesthetized using one or more drops of a topical anesthetic. Then, with the anticlog plunger 3 inserted into the drilling needle member 10, the drilling needle member 10 is coupled to a standard contra angle head of a dental drill 15 via the housing 1.

Figure 5:
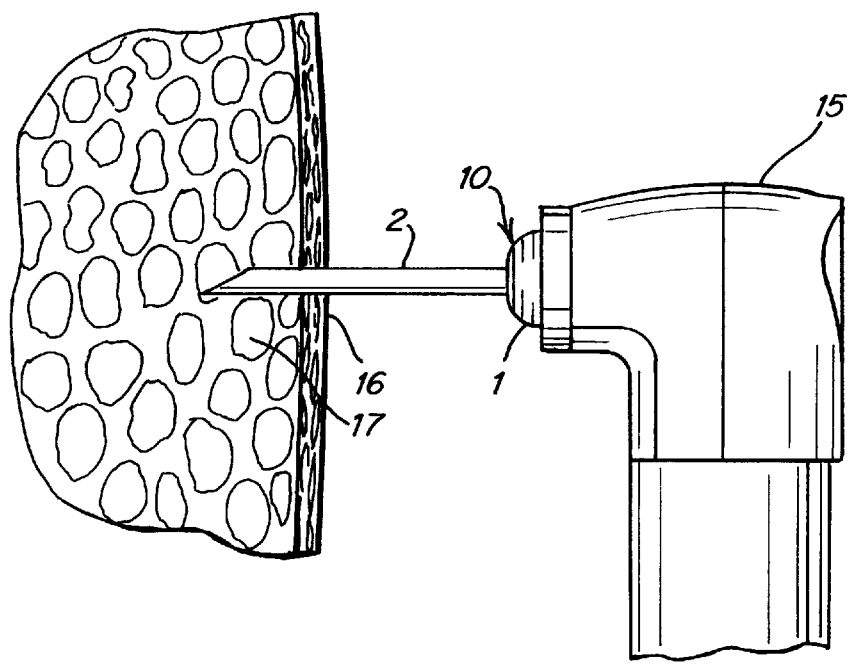
FIG. 5 is a perspective view of the drilling needle apparatus of the first embodiment in use during a first procedural step.

As shown in FIG. 5, the dental drill 15 is used to drive the drilling needle shaft 2 through the gingiva 16 and into the jawbone 17 perpendicular to the cortical plate of the jawbone 17. Preferably, the drilling needle shaft is rotated at around 20,000 rpm. Speeds of between about 10,000 and about 25,000 rpm could be used. The dental drill 15 is then uncoupled from the housing 1.

Figure 6:
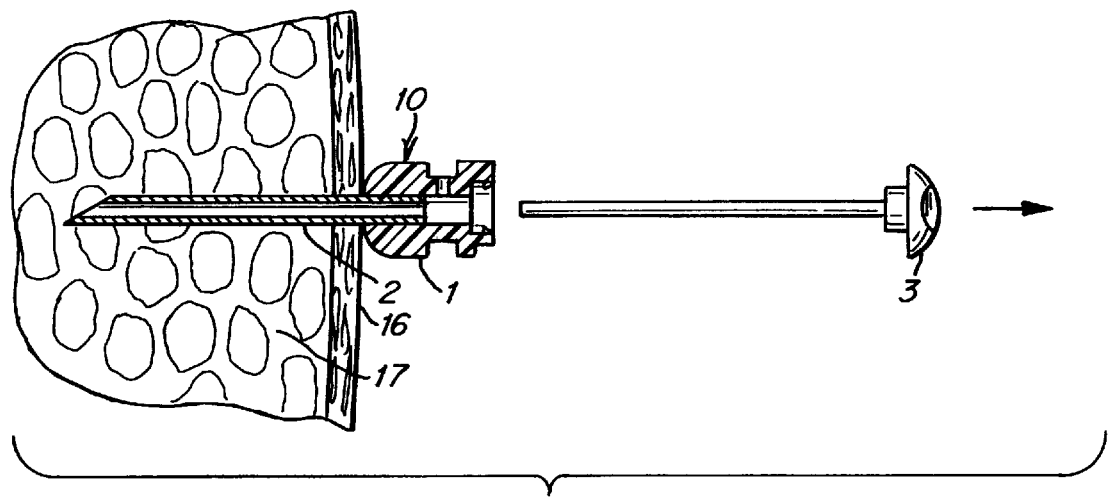
FIG. 6 is a perspective view of the drilling needle apparatus of the first embodiment in use during a second procedural step.

Next, as shown in FIG. 6, the anticlog plunger 3 is removed from the drilling needle member 10.

Figure 7:
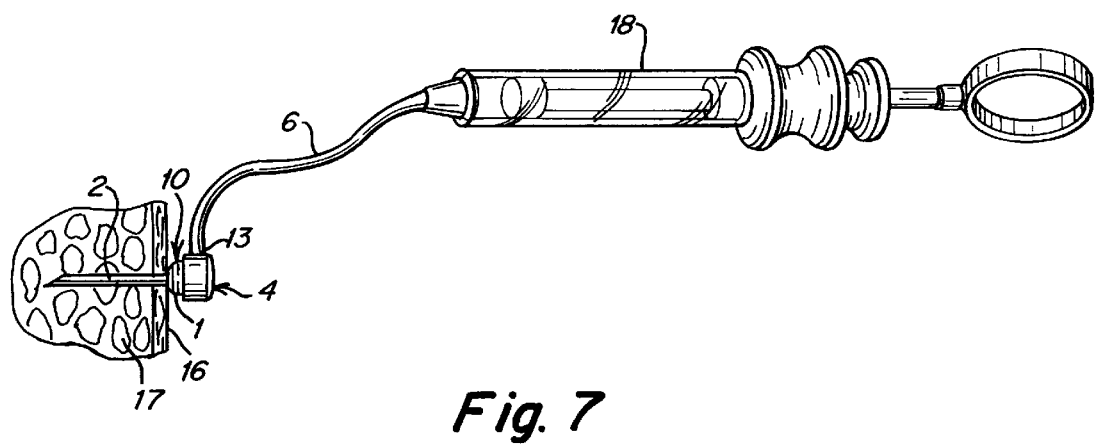
FIG. 7 is a perspective view of the drilling needle apparatus of the first embodiment in use during a third procedural step.

Next, as shown in FIG. 7, a syringe 18 is coupled to the cap 4 via flex tube 6, which is engaged with the nozzle 13 of the cap 4, and the cap 4 is engaged with the housing 1. As a result, a continuous liquid tight communication path is established from the syringe 18 through the flex tube 6 and the nozzle 13 into the housing 1 and through the drilling needle shaft 2. Anesthesia is then slowly injected directly into the jawbone via this communication path. The drilling needle member 10 preferably remains in the drilled-in position in the jawbone 17 during the dental procedure so that more anesthesia can be administered therethrough, as may be needed, during the procedure.

Figure 8:
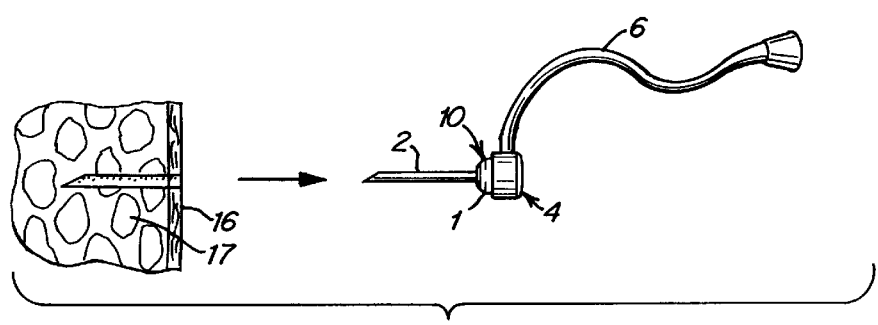
FIG. 8 is a perspective view of the drilling needle apparatus of the first embodiment in use during a fourth procedural step.

Finally, as shown in FIG. 8, the drilling needle shaft 2, housing 1 and cap 4 are removed from the jawbone 17 and may thereafter be discarded.

It should be appreciated that the first embodiment of the present invention provides a disposable delivery apparatus and method for intraosseously delivering dental anesthesia in a simple, easy and effective manner. In particular, it should be appreciated that the first embodiment of the present invention provides a disposable delivery apparatus and method for intraosseously delivering dental anesthesia which takes advantage of the power of a conventional dental drill for a creating sufficient force to achieve simple, easy and effective penetration of the jawbone, and which enables a communication path into the jawbone to be simply, easily and effectively established.

Thus, according to the intraosseous delivery apparatus and method of the first embodiment of the present invention, very rapid numbness limited only to the tooth to be treated may be achieved with significantly reduced amounts of anesthetic and essentially no post-operative numbness. In particular, the intraosseous delivery apparatus and method of the first embodiment of the present invention enables a safe and effective anesthetic effect to be achieved with approximately ten times less anesthesia than the widely practiced conventional mucous tissue injection technique.

A second embodiment of the present invention is shown in FIGS. 9–17. As shown in FIG. 9, a drill coupling member 100 according to the second embodiment comprises a shaft 101, an open housing 104 provided at one end of the shaft, and a connecting portion 103 provided at an opposite end of the shaft for establishing a connection to a conventional dental drill handpiece. The open housing 104 includes a first portion 105 having a round cross section, and a second portion 106 having a square cross section. The round cross section portion 105 and square cross section portion 106 can be clearly seen in FIG. 10, which shows a left side end view of the drill coupling member 100. As shown in FIG. 9, an anticlog needle 102 extends from the shaft 101 through the open housing 104. The anticlog needle 102 may be hollow as shown in FIG. 9, or solid, and the anticlog needle 102 may also be flexible or rigid. More specifically, the anticlog needle 102 may, for example, be a standard 27 gauge regular wall needle having an oblique cutting edge 116. The shaft 101, open housing 104 and connecting portion 103 of the drill coupling member 100, moreover, may be formed of a plastic material, with the anticlog needle 102 being insert molded in the shaft 101. Thus, when the drill coupling member 100 is connected to a dental handpiece, the entire assembly of the handpiece (not shown), the drill coupling member 100 and the anticlog needle 102 can be removed from the drilling needle member 108 (to be described below) in one motion.

FIGS. 11 and 12 are cross sectional views taken along lines 11—11 and 12—12 shown in FIG. 9, respectively, and FIG. 13 is a cross sectional view taken along line 13—13 shown in FIG. 10. As shown in FIG. 13, a friction grip member 107 may be molded as shown in FIG. 13, or a member such as an O-ring may be provided on the interior surface of the round cross-sectional portion 105 of the open housing 104.

Figure 14:
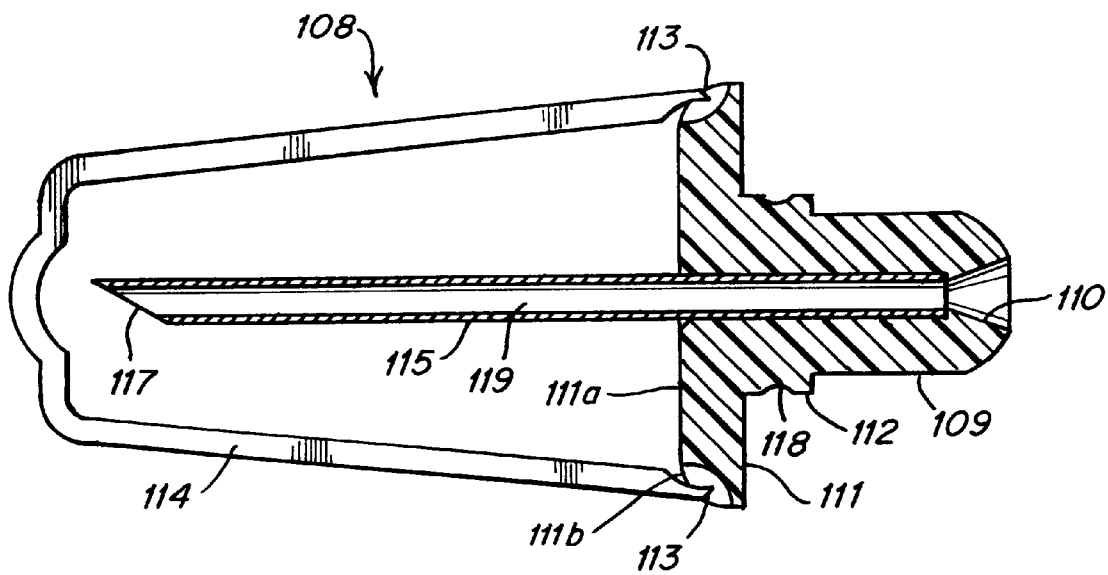
FIG. 14 is a sectional view of a drilling needle member according to the second embodiment of the present invention.

FIG. 14 is a sectional view of a drilling needle member 108 according to the second embodiment of the present invention. The drilling needle member 108 comprises a drilling needle housing 109 and a drilling needle shaft 115 extending therefrom. The drilling needle housing 109 has a flared opening 110 at one end portion thereof, and a press surface flange 111 at an opposite end portion thereof. The surface 111a of the housing 109 is preferably smooth so as to not to damage tissue of the patient when the device is installed or drilled into a bone of the patient. The surface 111a also has rounded edges 111b to further prevent damage to gum tissue of the patient. As shown in FIG. 14, the drilling needle housing 109 may also be provided with a boss 112 which may have a groove 118 provided therein. The friction grip protruding member 107 of FIG. 13 snappingly engages (due to the inherent resiliency of the plastic member) in the groove 118 to improve retention of the drilling needle member 108 in the drill coupling member 100. In addition, a drilling needle cap 114 may be coupled to the drilling needle housing 109 via break away points 113. The drilling needle shaft 115 includes a passageway 119 therein communicating with a delivery opening for delivering a fluid which is formed by oblique cutting edge 117. The drilling needle shaft may, for example, be a standard syringe-type needle having a 23 gauge thin wall, and the drilling needle housing 109 and drilling needle cap 114 may be formed of a plastic material, with the drilling needle shaft 115 being insert molded in the drilling needle housing 109.

Figure 15:
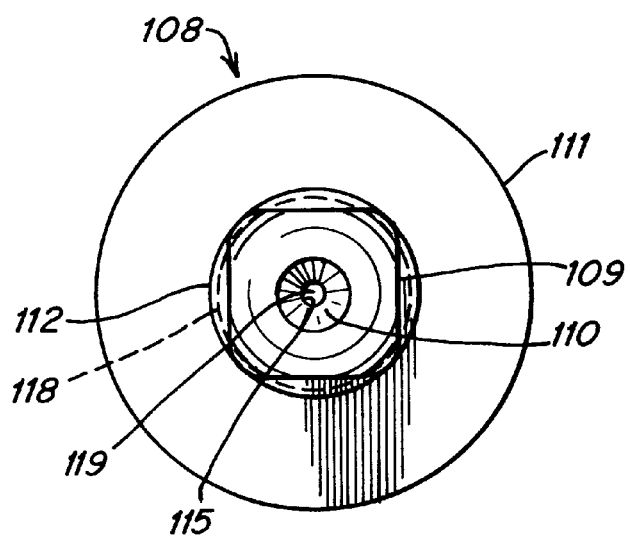
FIG. 15 is a right side end view of the drilling needle member shown in FIG. 14.

FIG. 15 is a right side end view of the drilling needle shown in FIG. 14. As shown in FIG. 15, the drilling needle housing 109 may have essentially a square cross section with rounded corners, and is dimensioned such that it can be frictionally fitted within the square cross sectional portion 106 of the open housing 104 of the drill coupling member 100. For example, the drilling needle housing 109 may be formed essentially in the shape of a square having a 2.50 mm legs, while the portion 106 of the open housing 104 of the drill coupling member 100 in which the drilling needle housing 109 is to be frictionally fitted may be formed in the shape of a square having 2.55 mm legs. Of course, drilling needle housing 109 and the portion 106 of the open housing 104 may also each be rectangular in shape, and/or may be formed in any compatible shapes such as oval or other non-round shapes, such that a rotational driving force may be applied therebetween without slippage therebetween.

FIG. 16 is a partial sectional view of the drill coupling member 100 and drilling needle member 108 according to the second embodiment of the present invention in a connected state. As shown in FIG. 16, the drilling needle member 108 is connected to the drill coupling member 100 such that the anticlog needle 102 is inserted through the flared opening 110 of the drilling needle member 108 and into the passageway 119 in the drilling needle shaft 115, and such that the drilling needle housing 109 of the drilling needle member 108 is fitted within the open housing 104 of the drill coupling member 100. The oblique cutting edges 116 and 117 of the anticlog needle and drilling needle shaft, respectively, may be offset as shown in FIG. 16 (in which position, the anticlog needle provides some cutting action and enhances performance of the drill), or they may be aligned together. In either case, the anticlog needle 102 will serve to prevent cuttings or other debris from entering the passageway 119 in the drilling needle shaft 115 during drilling. The friction grip member 107 provided on the interior surface of the round cross sectional portion 105 of the open housing 104 of the drill coupling member 100 is sealingly engaged with the groove 118 provided in the boss 112 provided on the drilling needle housing 109 of the drilling needle member 108, and the open housing 104 presses against flange 111 of the drilling needle member 108. The oblique cutting edges 116 and 117 of the anticlog needle and of the drilling needle are preferably ground 20–30 degrees relative to the longitudinal axes thereof. Other angles or drilling edge configurations could be used. Preferably, the assembly of the drilling needle and anticlog pin is rotated at about 20,000 rpm during the drilling procedure. However, speeds of about 10,000 to 25,000 rpm could be used with varying degrees of efficiency. Other speeds, for example below 10,000 rpm or above 25,000 rpm could also be used with varying degrees of efficiency, depending upon the specific application.

FIG. 17 is a cross sectional view taken along line 17—17 shown in FIG. 16. As shown in FIG. 17, the drilling needle housing 109 of the drill coupling member 100 is frictionally fitted against the square cross sectional portion 106 within the open housing 104 of the drill coupling member 100 so that a rotational driving force may be applied from the drill coupling member 100 to the drilling needle housing 109. While the open housing 104 is a "female" member, and the square cross sectional portion 106 is a "male" member, which together provide a coupling so that the members are non-rotational with respect to each other, the configurations could be reversed. That is, the housing 104 could have a projecting or male member, such as a square cross sectional portion, instead of the open female member, and the projecting portion 109 of square cross section could be replaced with an open or female portion which would non-rotationally engage with the male portion of the member 100. In this manner, the drilling needle 108 is non-rotationally coupled to the drill coupling member 100 in an equivalent manner, such that a rotational force applied to the drill coupling member 100 is transmitted to the drilling needle member, to enable drilling, as described hereinabove. Other arrangements for providing a non-rotational coupling between the drill coupling member 100 and the drilling needle member 108 can be used.

The procedural operations for applying anesthesia in accordance with the second embodiment of the present invention will now be described. The drill coupling member 100 is preferably pre-assembled to the drilling needle member 108, and the preassembled unit is connected to a conventional dental drill (handpiece). Alternatively, the drill coupling member 100 may be first connected to a conventional dental drill via the connecting portion 103, and the drilling needle member 108 may then be coupled to the drill coupling member 100 as described above. The cap 114 of the drilling needle member 108 is then broken off to expose the drilling needle shaft 115 with the anticlog needle 102 inserted therein. The dental drill is then used to apply a rotational driving force by via the drill coupling member 100 to the drilling needle housing 109 of the drilling needle member 108 so that the drilling needle shaft 115 with the anticlog needle 102 inserted therein is rotatingly driven to drill a hole in the jawbone or tooth of a patient. In addition, a pressing force may also be applied via the flange 111 of the drilling needle member 108 so as to assist the drilling operation. The pressing force and rotational driving force are applied until the flange 111 presses against or contacts the tooth or gums of the patient, thereby ensuring that the drilling needle member 108 has been fully inserted in the drilled hole.

Once the drilling operation is completed, the drill coupling member 100 is disengaged from the drilling needle member 108 in a manner such that the drilling needle shaft 115 is left inserted in the drilled hole. This may be achieved by exerting a forward pressing force on the outer edges of the flange 111 of the drilling needle member 108 while at the same time exerting a rearward withdrawal force on the drill coupling member 100. As mentioned above, during the drilling operation, the anticlog needle 102 prevents cuttings and other debris from entering the passageway 119 in the drilling needle shaft 115. Accordingly, upon withdrawal of the anticlog needle 102, a clear conduit into the interior of the tooth or bone of the patient is established via the passageway 119 in the drilling needle shaft 115 which remains inserted in the drilled hole. A conventional syringe may then be used to inject an anesthetic or other fluid into the interior of the tooth or bone of the patient via the passageway 119. More specifically, a needle extending from a conventional syringe is inserted through the flared opening 110 of the drilling needle member 108 and into the passageway 119 in the drilling needle shaft 115. The needle of the syringe must, of course, have a gauge smaller than the gauge of the drilling needle shaft 115 such that the needle of the syringe may be inserted into the passageway 119. For example, the needle of the syringe may, like the anticlog needle 102, be a standard 27 gauge regular wall needle.

Once the anesthetic or other fluid has been injected, the needle of the syringe is then withdrawn from the passageway 119 in a manner such that the drilling needle shaft 115 is again left inserted in the tooth or bone of the patient. The drilling needle shaft 115 and the drilling needle member 108 preferably remains in the inserted position in the bone during the entire dental procedure. Additional anesthetic or other fluid may then be applied, if and when necessary, via the passageway 119 in the drilling needle shaft which is left inserted in the tooth or bone of the patient. Accordingly, a direct, reusable communication path is established and maintained into the jawbone or tooth of the patient which enables simple reinjection of anesthetic or other fluid, if and when necessary, during performance of a dental procedure.

The above described advantageous effect of the second embodiment of the claimed present invention is enabled to be achieved because the drilling needle member 108 which is left inserted in the jawbone or tooth of the patient is sufficiently small and unobtrusive so as not to interfere with the dental procedure which is being performed. Preferably, the drilling needle member 108 projects no more than about 5 mm from the gum surface, when the device is used in dental applications. The drilling needle member 108 may therefore be left inserted in the jawbone or tooth of the patient throughout a dental procedure, and need only be removed once the dental procedure is completed. At the end of the procedure, in order to remove the drilling needle member 108 from the tooth or jawbone of the patient, the boss 112 on the drilling needle member may be gripped and pulled either manually or, for example, by a pliers-type tool or U-shaped tool which is adapted to grip the groove 118 provided in the boss 112.

Preferably, the members 100 and 108 are injection molded of polystyrene with 20% calcium carbon, with the respective needle members 115 and 102 insert molded therein. Other materials (such as other plastics) could be used in place of the polystyrene material.

Additional advantages and modifications will readily occur to those skilled in the art. Therefore, the invention in its broader aspects is not limited to the specific details, representative devices, and illustrated uses and examples shown and described herein. Accordingly, various features of the respectively disclosed embodiments can be used with other embodiments, and various modifications may be made without departing from the spirit or scope of the general inventive concept of the present invention as defined by the appended claims and their equivalents.

What is claimed is:

1. An intraosseous delivery apparatus comprising:
   a housing having a delivery opening through which a fluid may be introduced, said housing being shaped to be removably coupled to a drill for providing a bone penetration force;
   a drilling needle shaft extending from the housing and having a cutting edge for drilling a hole in a bone, said drilling needle shaft having a passageway extending therethrough which communicates with the delivery opening for delivering the fluid introduced into the housing directly into the hole drilled in the bone; and
   a cap which may be liquid tightly engaged with the housing, said cap including a nozzle to which a flex tube is engageable, and said nozzle communicating with the delivery opening in the housing when the cap and the housing are engaged so as to establish a communication path from the flex tube through the nozzle into the housing and through the passageway provided in the drilling needle shaft directly into the hole drilled in the bone.

2. The intraosseous delivery apparatus according to claim 1, further comprising a removable anticlog plunger having an anticlog pin extending therefrom, said anticlog plunger being insertable into the housing such that the anticlog pin fills the passageway in the drilling needle shaft and so that when the drilling needle shaft drills the hole in the bone, the anticlog pin prevents debris from entering into the passageway in the drilling needle shaft.

3. An intraosseous delivery method comprising the steps of:
   removably coupling a housing and a drill, said housing having a drilling needle shaft extending therefrom, and said drilling needle shaft having a passageway provided therein which communicates with a delivery opening provided in the housing;
   using the drill to provide a bone penetration force for causing the drilling needle shaft to drill a hole directly in a bone;
   removing the drill from the housing;
   liquid tightly engaging a cap with the housing after removing the drill from the housing, said cap including a nozzle to which a flex tube is engageable, and said nozzle communicating with the delivery opening in the housing when the cap and the housing are engaged so as to establish a communication path from the flex tube through the nozzle into the housing and through the passageway provided in the drilling needle shaft directly into the hole drilled in the bone; and introducing a fluid into the delivery opening in the housing and through the passageway provided in the drilling needle shaft so as to directly deliver the fluid into the hole drilled in the bone.

4. The intraosseous delivery method according to claim 3, further comprising:

an initial step of inserting a removable anticlog plunger having an anticlog pin extending therefrom into the housing prior to removably coupling the housing to the drill, such that the anticlog pin fills the passageway in the drilling needle shaft and so that when the drilling needle shaft drills the hole in the bone, the anticlog pin prevents debris from entering into the passageway in the drilling needle shaft; and an additional step of removing the anticlog plunger and the anticlog pin from the housing immediately after removing the drill from the housing and prior to liquid tightly engaging the cap with the housing.

5. An intraosseous delivery apparatus comprising:

a drill coupling member including a shaft portion, a housing provided at one end portion of the shaft portion, a connecting portion provided at an opposite end of the shaft portion for establishing a connection to a conventional dental drill, and a hollow anticlog needle extending from the shaft portion through the housing; and a drilling needle member including a drilling needle housing and a hollow drilling needle shaft extending from the drilling needle housing, said drilling needle member being adapted to be removably engaged with the drill coupling member by removably engaging the drilling needle housing of the drilling needle member with the housing of the drill coupling member, such that the hollow anticlog needle of the drill coupling member is inserted into the hollow drilling needle shaft of the drilling needle member;

wherein the drilling needle housing of the drilling needle member and the housing of the drill coupling member are shaped so that a bone penetration force may be applied therebetween for drilling a hole in a bone to insert the drilling needle member therein when the drilling needle member and the drill coupling member are engaged; and wherein said hollow drilling needle shaft is adapted to receive a needle of a syringe when the drilling needle member and the drill coupling member are disengaged and the drilling needle member is left inserted in the hole drilled in the bone, so that a reusable communication path through the hollow drilling needle shaft directly into the hole drilled in the bone is established through which fluid may be repeatedly injected.

6. The intraosseous delivery apparatus according to claim 5, wherein the hollow anticlog needle is dimensioned to substantially fill the hollow drilling needle shaft when the drilling needle member and the drill coupling member are engaged so that the hollow anticlog needle prevents debris from entering the hollow drilling needle shaft when the hole in the bone is drilled.

7. The intraosseous delivery apparatus according to claim 6, wherein the housing of the drill coupling member includes a distal portion have a round cross section, and the drilling needle housing of the drilling needle member includes a boss dimensioned to be received within the round cross sectional distal portion of the open housing of the drill coupling member.

8. The intraosseous delivery apparatus according to claim 7, further comprising a friction grip member provided on the round cross sectional distal portion of the housing of the drill coupling member, and a groove provided in the boss of the drilling needle housing of the drilling needle member, said friction grip member and said groove being dimensioned to sealingly engage each other when the drilling needle member and the drill coupling member are engaged.

9. The intraosseous delivery apparatus according to claim 5, wherein the housing of the drill coupling member includes an inner portion having a rectangular cross section, and the drilling needle housing of the drilling needle member includes a distal rectangular cross section portion dimensioned to be inserted into the rectangular cross sectional inner portion of the open housing of the drill coupling member, whereby the engaged housings are non-rotational relative to each other when engaged.

10. The intraosseous delivery apparatus according to claim 5, wherein the drilling needle housing of the drilling needle member includes a flange which is dimensioned to be larger than an outer circumference of the housing of the drill coupling member, said flange having a first side which is pressed toward the bone when the hole in the bone is drilled and a second side against which the drill coupling member may be pressed to apply a forward driving force.

11. The intraosseous delivery apparatus according to claim 5, wherein the drilling needle housing of the drilling needle member includes a flared opening through which the hollow anticlog needle of the drill coupling member and a needle of a conventional syringe may be inserted into the hollow drilling needle shaft.

12. The intraosseous delivery apparatus according to claim 5, wherein the drilling needle housing of the drilling needle member includes a cap covering the drilling needle shaft, said cap being coupled to the drilling needle housing via breakaway points so that the cap is securely coupled to the drilling needle housing and may be broken off to expose the drilling needle shaft.

13. The intraosseous delivery apparatus according to claim 12, wherein the drilling needle housing and the cap of the drilling needle member are formed of a plastic material, and the drilling needle shaft is insert molded in the drilling needle housing.

14. The intraosseous delivery apparatus according to claim 5, wherein the drilling needle shaft and the hollow anticlog needle each comprise an oblique cutting edge.

15. The intraosseous delivery apparatus according to claim 5, wherein the shaft portion, the housing of the drill coupling member and the connecting portion of the drill coupling member are formed of a plastic material, and the hollow anticlog needle is insert molded in the shaft portion.

16. The intraosseous delivery apparatus according to claim 5, wherein said housing of the drill coupling member comprises an open housing portion which receives therein a housing portion of said drilling needle member.

17. An intraosseous delivery method comprising the steps of:

removably coupling a drill coupling member to a drill, said drill coupling member including a shaft portion, a housing provided at one end of the shaft portion, a connecting portion provided at an opposite end of the shaft portion, and a hollow anticlog needle extending from the shaft portion through the housing; and removably engaging a drilling needle member with the drill coupling member such that a drilling needle housing of the drilling needle member is non-rotatably coupled to the housing of the drill coupling member and such that the hollow anticlog needle of the drill coupling member is inserted into a hollow drilling needle shaft extending from the drilling needle housing of the drilling needle member;

applying a bone penetration force from the drill via the drill coupling member to the drilling needle housing of the drilling needle member so that the hollow drilling needle shaft with the hollow anticlog needle inserted therein drills a hole in a bone;

disengaging the drill coupling member from the drilling needle member in a manner such that the hollow drilling needle shaft is left inserted in the hole drilled in the bone;

inserting a needle of a syringe into the hollow drilling needle shaft left inserted in the hole drilled in the bone; and introducing a fluid from the syringe directly into the hole drilled in the bone via the hollow drilling needle shaft.

18. The intraosseous delivery method according to claim 17, further comprising a step of removing the needle of the syringe from the hollow drilling needle shaft in a manner such that the hollow drilling needle shaft is again left inserted in the hole drilled in the bone.

19. The intraosseous delivery method according to claim 17, wherein the hollow drilling needle shaft is left inserted in the hole drilled in the bone throughout a dental procedure, and wherein fluid is repeatedly injected directly into the hole drilled in the bone via the hollow drilling needle shaft, if and when necessary, during the dental procedure.

20. The intraosseous delivery method according to claim 17, further comprising a step of breaking off a cap covering the drilling needle shaft from the drilling needle housing of the drilling needle member so as to expose the drilling needle shaft prior applying the bone penetration force.

21. The intraosseous delivery method according to claim 17, further comprising a step of removing the hollow drilling needle shaft from the hole drilled in the bone by exerting a pulling force on a boss provided on the drilling needle housing of the drilling needle member.

22. The intraosseous delivery method according to claim 17, wherein said housing of the drill coupling member comprises an open housing portion which receives therein a housing portion of the drill needle member.

* * * * *